United States Patent [19]

Chater

[11] Patent Number: Plant 5,418

[45] Date of Patent: Mar. 19, 1985

[54] POMEGRANATE CV. ARMCHAT

[75] Inventor: Sasszin J. Chater, Camarillo, Calif.

[73] Assignee: Armstrong Nurseries, Inc., Ontario, Calif.

[21] Appl. No.: 505,490

[22] Filed: Jun. 17, 1983

[51] Int. Cl.[3] ..... A01H 5/03

[52] U.S. Cl. ..... Plt/33

[58] Field of Search ..... Plt./33

*Primary Examiner*—Robert E. Bagwill

*Attorney, Agent, or Firm*—Synnestvedt & Lechner

[57] ABSTRACT

A new variety of pomegranate bearing edible fruits with seed pulp that is very sweet even when fruits are small and green; the fruits maturing in two to three or more ripening periods from mid-August through mid-November.

2 Drawing Figures

This invention relates to a new variety of fruiting pomegranate, *Punica granatum*, cv. Armchat, which bears normal-appearing fruits that contain many seeds enclosed in a juicy, edible pulp which is very sweet to the taste even when the fruits are small, green and very immature. It is a summer and fall bearer, producing mature fruits from approximately mid-August to about mid-November in southern California. Its hardiness has not yet been tested.

The new variety is a chance seedling arising from a pomegranate cultivar commonly grown in home gardens in Lebanon. The seed was planted by the inventor in his home garden in southern California. During the first fruiting and in all subsequent fruitings of this new seedling the inventor found that even from the time the fruits are still small, in fact no larger than 1½ inches in diameter, the seed pulp is quite sweet-flavored and highly palatable. The inventor propagated several more plants from the original by rooting cuttings in his home garden. These plants have now matured, and their characteristics are identical to the original seedling.

While fruits of the new seedling variety are only about half the size of fruits of the parent variety, they are more highly colored, the parent variety being nearly white and devoid of any notable reddish blush. The new variety is also thicker-skinned and much less susceptible to bruising and spoilage than was its parent.

In comparison with 'Wonderful,' the main fruiting pomegranate available in the United States, this new variety has somewhat lighter-colored orange-red flowers and somewhat less red pigment in the fruit skin and the seed pulp. The fruits of 'Wonderful' have an exposed apex with the sepals spreading outward while the fruits of the new cultivar have a concealed apex with the sepals drawn rather tightly closed at maturity. 'Wonderful' produces one crop of mature fruits a year in mid-fall, while the new cultivar usually produces two to three crops of mature fruit each year in southern California, beginning in mid-summer and continuing through late fall.

The accompanying drawings show, in full color, three mature fruits growing on a mature plant, with immature, yet already edible fruits in the background, plus twigs with leaves, flower buds and blossoms along with open sections, cut in both horizontal and vertical planes, revealing the pulp-covered seeds.

In the description that follows, designations beginning with capital letters are color values taken from The R.H.S. Colour Chart put out by The Royal Horticultural Society London.

BUSH

The bush is of average size for pomegranates, growing normally as an 8–10 foot fountain-shaped shrub. It may easily be trained as a small tree or espaliered or shaped in other ways. Winter hardiness is as yet untested. In southern California, even near the coast, it regularly produces two to three average crops of fruit per year.

Trunk: The normal habit of this variety is to produce several main trunks with moderately smooth bark.

Branches: The branches are somewhat willowy and pliable, sometimes nearly four-sided and slightly winged. The color varies between 147C and 195C.

New shoots: New shoots are four-sided and slightly winged. They are also willowy and pliable. The color is between 144B and 161B, with wing color near 47C.

Leaves: The leaves are simple, linear-oblong, semi-glossy and mostly opposite, with a smooth margin, acute base and acute apex. In size, shape, distribution and color they are similar to leaves of 'Wonderful.' Leaf color on both the upper and under surfaces of immature foliage is between 141A and 146A, heavily suffused with near 175B. The upper surface of mature foliage is between, but brighter than, 139A and 146A in color, while the color of the under surface is near 146B.

Flowers: The flowers are very showy and of medium size, being approximately 2 inches in diameter, 1½ inches in length and comprising usually 5 to 7 nearly round to oval petals uniformly colored near 33B on both sides of each petal. The petals are arranged regularly. There is one pistil approximately ½ inch in length; the style is near 4B in color while the stigma is near 150B in color. There are many average size anthers, near 10B in color, which are borne on slender filaments near 32A in color. The outside of the cup is between 32A and 34A in color as the sepals begin to open, while the color on the inside surfaces of the cup is near 32C at the same time. The 5 to 7 sepals are approximately ⅜ inch long, of the same color values on the outer and inner surfaces as the cup, and are alternate to the petals. Usually 3 to 5 flowers form in clusters near the ends of the branches, generally in two to three or more blooming periods beginning in early spring and continuing through summer and sometimes into fall in southern California.

FRUIT

The fruit is produced in moderate quantities in each of two to three or more fruit-setting periods in the spring and summer. While the pulp surrounding the many seeds in each fruit is sweet-tasting and edible within 4 to 6 weeks after pollination, the first fruits generally mature beginning in mid-August in southern California and continuing through November. When fully mature, the globose fruits are approximately $3\frac{1}{2}$ inches long and $3\frac{1}{4}$ or more inches in diameter with connivent sepals. The skin color of fruits produced in the inventor's home garden, which is near the California coast, is near 18B, blushed, streaked, blotched and speckled rather heavily with near 45B. The flesh is thick and between 2C and 4D in color.

The numerous seeds are approximately $\frac{1}{4}$ inch long and near 159A in color. They are covered with a thick, juicy, translucent pulp which is between 42A and 47C in color. The flavor of the pulp is mild but very sweet.

The keeping quality of the fruit is average; the use is dessert.

The plant and fruit display average resistance to diseases and pests.

I claim:

1. A new and distinct variety of fruiting pomegranate, substantially as herein illustrated and described, said variety being characterized in the very sweet quality of its seed pulp even in young immature fruits, the fruits of said variety ripening from mid-summer through late fall.

* * * * *

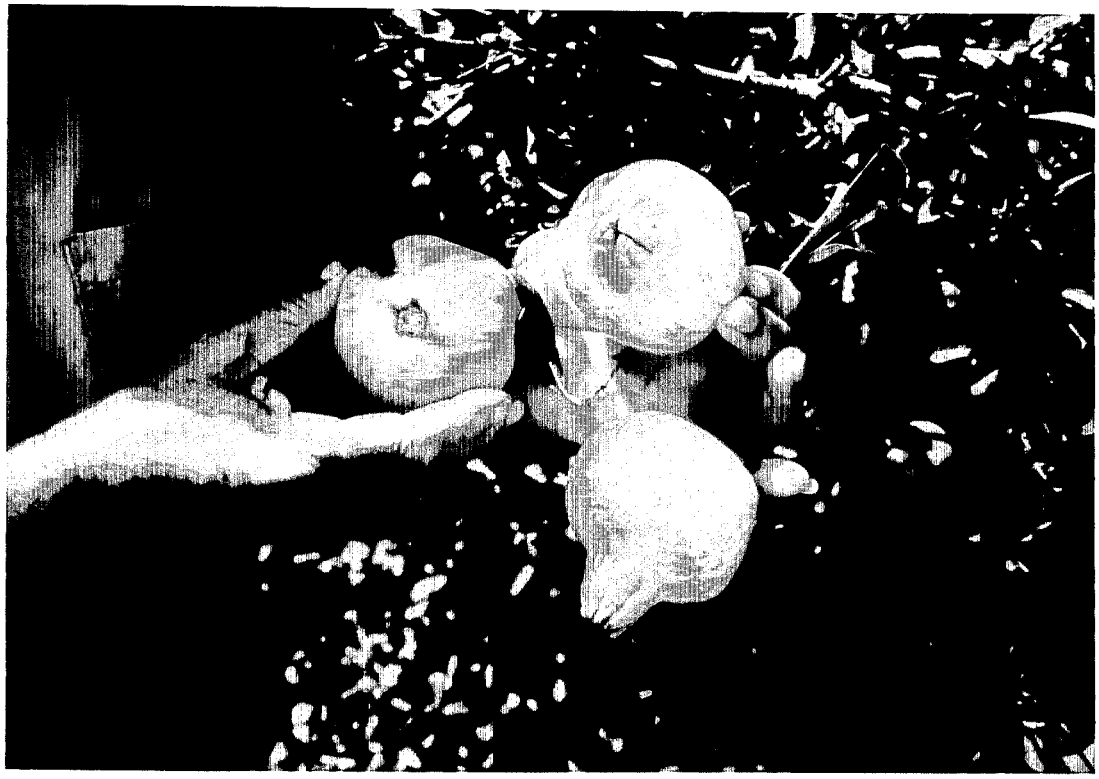
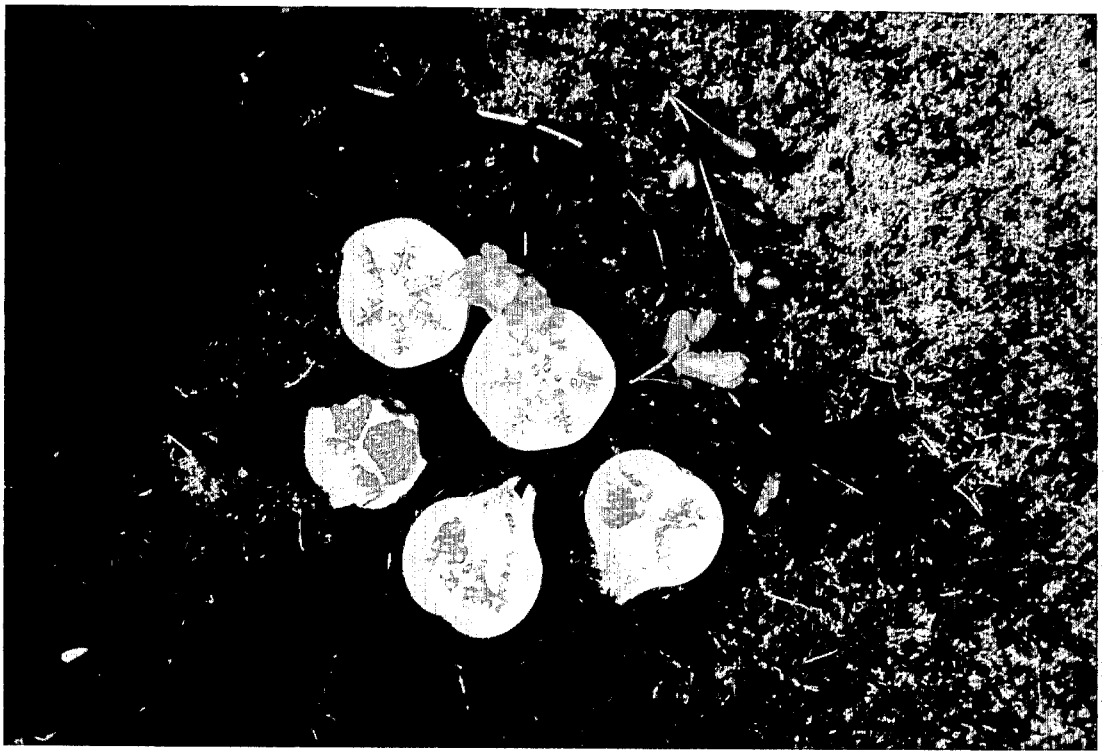

UNITED STATES PATENT AND TRADEMARK OFFICE

CERTIFICATE OF CORRECTION

PATENT NO. : Plant 5,418

DATED : March 19, 1985

INVENTOR(S) : Sassin J. Chater

It is certified that error appears in the above—identified patent and that said Letters Patent is hereby corrected as shown below:

On the title page, Item [757] the inventor's name reading "Sasszin J. Chater" should read --Sassin J. Chater--.

Signed and Sealed this

Sixth Day of August 1985

[SEAL]

*Attest:*

DONALD J. QUIGG

*Attesting Officer* *Acting Commissioner of Patents and Trademarks*